United States Patent [19]

Disteldorf et al.

[11] 4,283,535
[45] Aug. 11, 1981

[54] METHOD FOR THE PRODUCTION OF 2,4,6-TRIKETOHEXAHYDROTRIAZINES

[75] Inventors: Josef Disteldorf; Werner Hübel; Elmar Wolf, all of Herne, Fed. Rep. of Germany

[73] Assignee: Chemische Werke Huls AG, Fed. Rep. of Germany

[21] Appl. No.: 38,692

[22] Filed: May 14, 1979

[30] Foreign Application Priority Data

May 13, 1978 [DE] Fed. Rep. of Germany ....... 2821109

[51] Int. Cl.³ .......................................... C07D 251/34
[52] U.S. Cl. ..................................... 544/193; 544/222
[58] Field of Search ................. 544/222, 193

[56] References Cited

U.S. PATENT DOCUMENTS

| | | | |
|---|---|---|---|
| 3,517,002 | 6/1970 | Heiss | 544/222 |
| 3,619,338 | 11/1971 | Gilman | 544/222 |
| 3,641,024 | 2/1972 | Argabright et al. | 544/222 |
| 3,779,940 | 12/1973 | Argabright et al. | 544/222 |
| 3,840,496 | 10/1974 | Argabright et al. | 544/222 |
| 3,852,220 | 12/1974 | Kimmel et al. | 544/222 |
| 3,919,218 | 11/1975 | Schmitt et al. | 544/222 |
| 4,145,544 | 3/1979 | Kuehn | 544/222 |

*Primary Examiner*—John M. Ford
*Attorney, Agent, or Firm*—Oblon, Fisher, Spivak, McClelland & Maier

[57] ABSTRACT

A method of preparing 2,4,6-triketohexahydrotriazines which comprises catalytically trimerizing an organic isocyanate at 60°–150° C. in an inert, polar solvent present in an amount of 5–40 weight % with respect to the quantity of said isocyanate, in the presence of 0.1–5 weight % of a catalyst of the formula

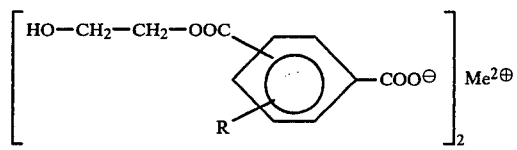

or hydrated derivatives of said catalyst, wherein R is selected from the group consisting of hydrogen and $C_1$–$C_4$ alkyl, and $Me^{+2}$ is a bivalent metal cation; interrupting the trimerization at a conversion of about 50% by cooling; and then isolating the 2,4,6-triketohexahydrotriazine.

6 Claims, 2 Drawing Figures

METHOD FOR THE PRODUCTION OF 2,4,6-TRIKETOHEXAHYDROTRIAZINES

BACKGROUND OF THE INVENTION

1. Field of the Invention

The present invention relates to the trimerization of organic isocyanates using an improved catalyst.

2. Description of the Prior Art

The trimerization of organic isocyanates is a known reaction. As catalysts for the trimerization of organic isocyanates there are described in the literature a great number of chemically very diverse compounds. Thus, there can be used as trimerization catalysts metal compounds from the salt and base groups and homopolar metal compounds, like naphthenates, Na-benzoate in dimethylformamide (DMF), alkaline-earth acetates, formates and carbonates, metal alkoxides, $AlCl_3$ and Fe-acetylacetonate. These are only partially separable, if at all, from the isocyanurate reaction products and only with great difficulty. The catalysts more likely remain in the reaction product.

This is naturally a great disadvantage, especially when one has to deal with an isocyanurate produced by the trimerization of a diisocyanate. In heating such products, the free NCO-groups of these isocyanurates continue to react in the presence of the trimerization catalyst. Higher molecular weight polyisocyanates containing isocyanurate rings are formed. With advancing reaction there is even cross-linking. Thus it is clear that catalyst-containing isocyanurates, which also contain NCO-groups bound by alkylene groups to the triazine ring, can hardly be used for the desired further reactions with alkohols or amines.

The aim in any process leading to isocyanurates (from polyisocyanates) must therefore be the complete elimination or neutralization of the catalyst after the trimerization. This can be achieved by using readily volatile basic compounds, like tertiary amines or phosphines, as trimerization catalysts. The disadvantage in using these compounds is, of course, that they (tertiary phosphines) catalyze not only the trimerization but also, in part, the dimerization of the isocyanates. Further, it must be noted that tertiary amines while catalyzing very well the trimerization of aromatic isocyanates, show no catalytic effect for aliphatic or cycloaliphatic isocyanates. Thus, for example, the trimerizations of hexamethylenediisocyanate (HDI), 2,2,4- or 2,4,4-trimethylhexamethylene diisocyanate-1,6 (TMDI); 3-isocyanatomethyl-3,5,5-trimethyl-cyclohexylisocyanate, also called isophorone diisocyanate (IPDI), or 3(or 4), 8(or 9)-diisocyanato-methylnorbornane (NDI) suceed neither with triethylamine nor with dimethylbenzylamine nor with 1,4-diazabicyclo[2.2.2]octane. These aliphatic or cycloaliphatic isocyanates however can be readily trimerized with Na-benzoate in DMF (Chemical Abstr. 60, 8332 (1963)) or with Na-phenolates in n-butylacetate (GB-PS 1,386,399). The great disadvantage of this just-mentioned method is the catalyst elimination from the reaction product. Na-benzoate as well as Na-phenolate must be filtered out from the reaction product after trimerization of the diisocyanate. This filtration leads to difficulties inasmuch as one has to deal with very finely crystalline (Na-benzoate particle sizes $<2\mu$) relatively slimy (Na-phenolate) precipitates.

A need therefore continues to exist for a method for producing 2, 4, 6-triketohexahydrotriazines by catalytic trimerization with a catalyst that does not give rise to the aforementioned problems.

SUMMARY OF THE INVENTION

It has now been found, surprisingly, that the problems with catalyst removal, as in the case of trimerization with Na-benzoate and Na-phenolate, do not arise when the method for producing 2,4,6-triketohexahydrotriazines by catalytic trimerization of organic isocyanates at elevated temperature is carried out by trimerization in the presence of a catalyst of the formula:

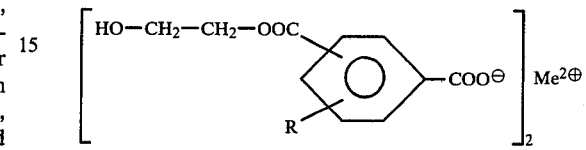

where R is hydrogen or a $C_1$-$C_4$-alkyl radical and Me is a bivalent metal cation, and its hydrated derivatives, in the range of 0.1-5 wt.%, preferably 0.5-3 wt.%, and in an inert, polar solvent in an amount of 5-40 wt.%, preferably 10-20 wt.%, with respect to the amount of isocyanate used at temperatures of 60°-150° C., preferably 80°-130° C.; the reaction is stopped at about 50% conversion by cooling, and the resultant isocyanurate is finally isolated by known means.

The catalysts of the invention and their production are known. They are described in the literature as reaction partners of diisocyanates for the production (in DMF) of "metal-containing polyurethanes" (H. Matsuda, J. Poly. Sci. 12 (1974) 455-468). It was therefore all the more astounding that these compounds are able to catalyze the trimerization of isocyanates at significantly lower concentrations.

BRIEF DESCRIPTION OF THE DRAWINGS

A more complete appreciation of the invention and many of the attendant advantages thereof will be readily obtained as the same becomes understood by reference to the following detailed description when considered in connection with the accompanying drawings, wherein.

DESCRIPTION OF THE PREFERRED EMBODIMENTS

Figure 1:
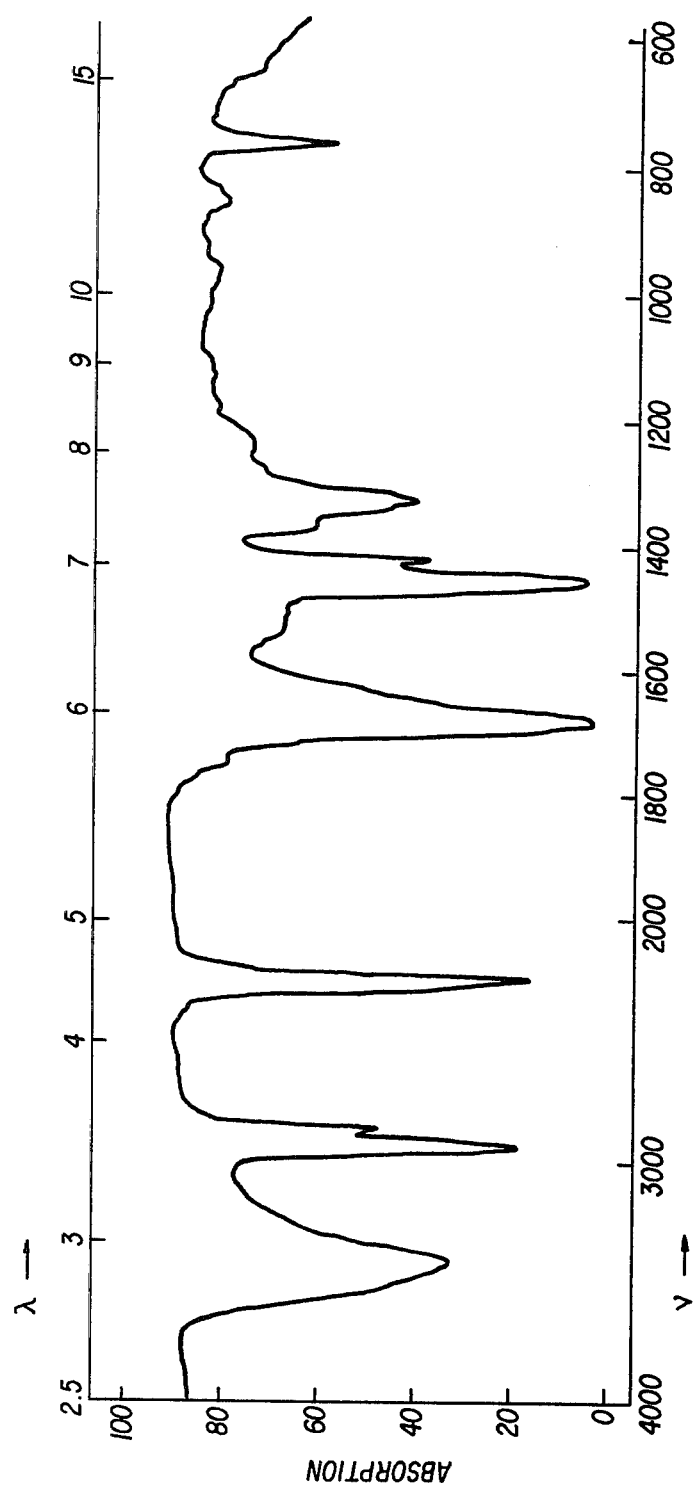
FIG. 1 is the infra-red spectrum of the trimer obtained by Example 1.

Suitable as starting material for the method of the invention are all mono-and polyisocyanates, like aliphatic, cycloaliphatic, araliphatic, arylsubstituted aliphatic and/or aromatic diisocyanates, as described for instance in Houben-Weyl, Methoden der Organischen Chemie, vol 14/2, pp. 61-70 and in the article by W. Siefken in Justus Liebig's Annalen der Chemie 562, 75-136. If one uses di- or other polyisocyanates, there can then be obtained corresponding isocyanate-group-containing isocyanurates which are of considerable technological importance. Thus, for example, aliphatic isocyanurates from diisocyanates in combination with hydroxyl-group-containing compounds are outstandingly suited for the production of clear and pigmented polyurethane two-component lacquers, distinguished by fast drying and good light stability.

Suitable isocyanates are, for example, monoisocyanates like methyl isocyanate, ethyl isocyanate, propyl isocyanate, n-butyl isocyanate, isohexyl isocyanate, dodecyl isocyanate, oleyl isocyanate, stearyl isocyanate, cyclohexyl isocyanate, 2-chlorethyl isocyanate, 2-cyanoethyl isocyanate, 6-chlorohexyl isocyanate, isocyanatoacetic ethyl ester, propyletherpropyl isocyanate, benzyl isocyanate, phenylethyl isocyanate, or the like; diisocyanates like methane diisocyanate, butane-1,1-diisocyanate, 1,2-ethylene diisocyanate, butane-1,2-diisocyanate, transvinylene diisocyanate, propane-1,3-diisocyanate, 1,4-tetramethylene diisocyanate, 2-butene-1,4-diisocyanate, 2-methylbutane-1,4-diisocyanate, pentane-1,5-diisocyanate,2,2-dimethylpentane-1,5-diisocyanate,1,6-hexamethylene diisocyanate, 1,1'-dinaphthyl-2,2'-diisocyanate, 2,2,4- or 2,4,4-trimethyl-hexamethylene diisocyanate-1,6(TMDI), heptane-1,7-diisocyanate, octane-1,8-diisocyanate, nonane-1, 9-diisocyanate, decane-1,10-diisocyanate, 1,12-dodecane diisocyanate, ω, ω'-diisocyanatodi-n-propylether, dimethylsilane diisocyanate, diphenylsilane diisocyanate, the esters of 2,6-diisocyanatocaproic acid like methyl-, methoxymethyl-, 1,2-dichloropropyl- and isopropyl ester; the corresponding diesters of 2,4-diisocyanatoglutaric acid, 2,5-diisocyanatoadipic acid, 2,6-diisocyanatopimelic acid, 2,7-diisocyanatosuberic acid, 2,9-diisocyanatosebacic acid, cyclobutane-1,3-diisocyanate, di-(isocyanatomethyl)cyclobutane, cyclohexane-1,3- and 1,4-diisocyanate, ω, ω'-1,4-dimethylcyclohexane diisocyanate, 3-isocyanatomethyl-3,5,5-trimethyl-cyclohexyl isocyanate, also called isophorone diisocyanate and abbreviated as IPDI, decahydro-8-methyl-(1,4-methanonaphthalene-2(or 3),5-ylenedimethylene diisocyanate, decahydro-4,7-methano-indane-1(or 2), 5(or 6)-ylenedimethylene diisocyanate, hexahydro-4,7-methanoindane-1(or 2), 5(or 6)-ylene diisocyanate, hexahydro-1, 3- or 1,4-phenylene diisocyanate,2,4- and 2,6-hexahydrotoluylene diisocyanate, hydrated diphenylethane diisocyanate, hydrated diphenylpropane diisocyanate, hydrated diphenylbutane diisocyanate, ω, ω'-1,3-dimethylbenzene diisocyanate, ω, ω'-1,4-dimethylcyclohexane diisocyanate,1-isopropylbenzene-2,4-diisocyanate, 1-chlorobenzene-2,4-diisocyanate,1-fluorobenzene-2,4-diisocyanate, 1-nitrobenzene-2,4-diisocyanate,1-chloro-4-methoxybenzene-2,5-diisocyanate, azobenzene-4,4'-diisocyanate, benzeneazonaphthalene-4,4'-diisocyanate, 2,4'-4,4'-diisocyanatodiphenyl, diphenylether-4,4'-diisocyanate, diphenylether-2,4-diisocyanate,4,4'-diisocyanato-3,3'-dichlorodiphenyl, 4,4'-diisocyanato-2,3'-or 3,3'-dimethoxy-diphenyl, 4,4'-diisocyanato-3,3'-dimethyl-diphenyl,4,4'-diisocyanato-3,3'-diphenyl-diphenyl,4,4'-diisocyanato-diphenylmethane, 3,3'-dimethoxydiphenylmethane-4,4'-diisocyanate, 4,4'-dimethoxyphenylmethane-3,3'-diisocyanate, naphthalene-1,4-, 1,5- or 3,5-diisocyanate, ω, ω'-1,4-dimethylnaphthalene diisocyanate, ω, ω'-1,5-dimethylnaphthalene diisocyanate, 1,1'-naphthyl-2,2'-diisocyanate, toluylene diisocyanates, toluylene-2,4-or 2,6-diisocyanate, diphenylsulfide-4,4'-diisocyanate, diphenylsulfone-4,4'-diisocyanate, benzophenone-3,3'-diisocyanate, fluorene-2,7-diisocyanate, anthraquinone-2,6-diisocyanate, pyrene-3,8-diisocyanate, chrysene-2,8-diisocyanate, N, N'-(4,4'-dimethyl-3,3'-diisocyanatodiphenyl)-uretdion, m- or p-xylylene diisocyanate, or even the triisocyanates like 1, 6, 11-triisocyanatoundecane, 2, 4, 4'-triisocyanato-diphenyl ether, 4,4',4"-triisocyanato-triphenyl methane and tris-(4-isocyanatophenyl)-thiophosphate as well as any mixtures of these isomers. Other suitable isocyanates are described in the cited article in the Annalen on p. 122 ff. Mixtures of the mentioned isocyanates can also be used.

Especially preferred as a rule, are the readily available aliphatic, cycloaliphatic or aromatic diisocyanates and in particular 3-isocyanatomethyl-3,5,5-trimethylcyclohexyl isocyanate and 2,4-toluylene diisocyanate as well as their isomeric mixtures.

The catalysts of the invention are used in quantities of 0.1–5 wt.%, preferably 0.5–3 wt.% with respect to the amount of isocyanate used. Prerequisite for the effectiveness of the catalyst, of course, is complete or at least partial solubility in an organic solvent, which naturally is also soluble in the isocyanate to be trimerized.

The preparation of the catalyst of the invention can proceed, for example, according to directions given in J. Polym. Sci. 12 (1974) 456. Thus, for instance, phthalic anhydride is converted in the presence of a catalyst selected from the group of tertiary amines, e.g., N, N-dimethylbenzylamine with ethylene glycol in a first reaction step to mono-(hydroxyethyl)-phthalate. In a further reaction step the acid ester, i.e., mono-(hydroxyethyl)-phthalate, is then neutralized with an alkaline-earth oxide, for example, to the corresponding alkaline-earth mono-(hydroxyethyl)-phthalate. Among bivalent metal cations are understood those of the alkaline earth metals, like magnesium and calcium, as well as zinc and tin.

As solvents are to be considered mainly strongly polar ones like dimethyl formamide, dimethyl sulfoxide or even hexamethyl phosphoric triamide. The higher the solubility of the catalyst in the solvent the lower is the concentration of the solvent (relative to the isocyanate present). The solvent is used in amounts of 5–40 wt.%, preferably 10–20 wt.%.

For production of the isocyanurates by the method of the invention, starting with the isocyanate to be trimerized the solvent is added in amounts of 5–40 wt.%, preferably 10–20 wt.%, and the catalyst in amounts of 0.1–5 wt.%, preferably 0.5–3 wt.%, and the mixture is warmed to a temperature between 60° and 150° C., preferably 80°–130° C. The rate of conversion of the isocyanate to the isocyanurate is controlled by determination of the NCO-content of the reaction mixture.

For production of the monomer-free isocyanurate it has proven expedient to trimerize the isocyanate only partially, i.e., to stop the reaction after about 50% conversion by cooling to room temperature, and by separating in a second reaction step the free isocyanate and solvent from the isocyanurate by thin-film distillation.

If the boiling points of the isocyanate and solvent are very far apart, then it is very advantageous for the method of the invention to separate the two components individually. This is done in a multi-step thin-film evaporation. The distilled-off isocyanate as well as the distilled off solvent can be reused for trimerization.

Further objects of the invention are isocyanatoisocyanurates of the following structure:

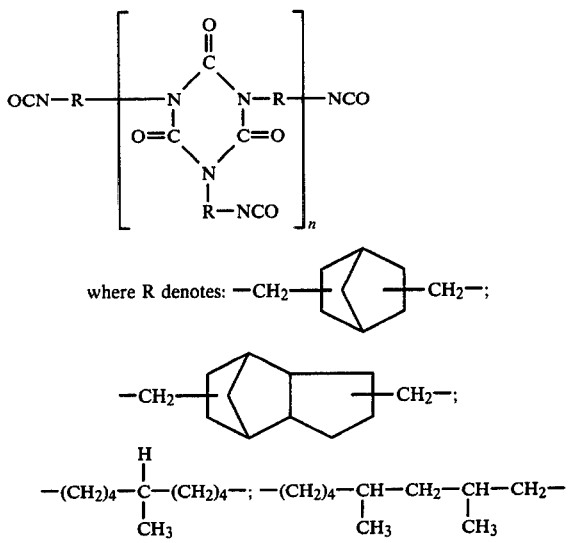

and n is an integer, preferably from 1 to 5.

Surprisingly, these isocyanurates have not yet been described in the literature.

The isocyanatoisocyanurates produced by the method of the invention from diisocyanates are quite soluble in the usual lacquer solvents like xylene, ethylglycol acetate, butyl acetates or the like. These solutions of isocyanatoisocyanurates are clear and do not change even in storage. The isocyanurates are valuable initial products.

The method of the present invention will be illustrated by the following examples given for purposes of illustration only and which are not intended to be limiting thereof:

A. Preparation of the catalyst

1. To 248.3 parts by wt. (4 moles) of ethylene glycol and 1.14 parts by wt. of N,N-dimethylbenzylamine at 70° C. there were added within 2 hours 118.5 parts by wt. (0.8 moles) of phthalic anhydride. After addition of the phthalic anhydride the reaction mixture was kept at 70° C. for another 2 hours. It was then cooled and 90 parts by wt. of acetone were added. To this solution at room temperature were added during about 30 minutes of intense stirring, 15.3 parts by wt. of MgO. After addition of the MgO the reaction mixture was kept at room temperature for another 20 minutes and then warmed to 60° C. for 2 hours. A white precipitate formed which was filtered, washed several times with acetone and then dried at 60° C. in a vacuum chamber.

The yield was 70% with respect to the amount of phthalic anhydride used.

2. The preparation of other salts of bivalent metal cations of the monohydroxyethyl-phthalic acids and their hydrated derivatives can be carried out analogously.

B. Trimerization of isocyanates by the method of the invention

EXAMPLE 1

500 parts by wt. of TCDI, 2.5 parts by wt. of Ca salts of monohydroxyethyl-phthalate as catalyst, prepared according to the directions in A₁, and 100 parts by wt. of dimethyl formamide (DMF) were mixed and heated to 130° C. After 1 hour the NCO-content of the reaction solution was 21.6%. The solution was then quickly cooled to 60° C. At this temperature the reaction mixture was largely freed of DMF in the spinner-evaporator (at about 133 Pa). To remove the unconverted TCDI and the slight remainder of DMF, the reaction mixture was distilled at 210° C./6.7 Pa in the thin-film evaporator. The residue had an NCO-content of 11.3% and a monomer content of <0.5%. The viscosity of the reaction product at 120° C. was 400Pa.S, at 140° C. it was 100 Pa.S.

The IR spectrum of the reaction product is given in FIG. 1.

EXAMPLE 2

500 parts by wt. of TCDI, 3 parts by wt. of the catalyst of the Ca salt of section A, and 30 parts by wt. of DMF were combined at room temperature and then heated to 120° C. After 50 minutes the NCO-content of the reaction solution was 23%. Thereupon the reaction solution was quickly cooled to 60° C. and treated as described in Example 1.

The reaction product (residue from the thin-film distillation) had an NCO-content of 11.6% and a monomer content of <0.6%. Its viscosity at 120° C. was 380 Pa.S and at 140° C. it was 96 Pa.S.

EXAMPLE 3

1000 parts by wt. of IPDI, 200 parts by wt. of DMF and 1 part by wt. of catalyst as in A, were mixed and then heated to 130° C. After 3 hours at 130° C. the reaction solution had an NCO-content of 17.8%. When this NCO-content had been reached the reaction mixture was cooled to 60° C. and, as already described in Examples 1 and 2, freed of the solvent (DMF). The almost DMF-free IPDI-containing IPDI-isocyanurate mixture was then subjected to the thin-film evaporation at 190° C./6.7 Pa. The distillation residue (reaction product) had an NCO-content of 17.4%, a monomer content of <0.5% and a viscosity at 120° C. of 140 Pa.s and at 140° C. of 41 Pa.s.

The reaction product (% NCO:17.4) dissolved in a xylene/ethylglycol acetate mixture to form a clear 70 wt.% solution with a viscosity of 1.35 Pa.s at 25° C.

EXAMPLE 4

500 parts by wt. of NDI, 130 parts by wt. of DMF and 5 parts by wt. of catalyst as in section A, were mixed and then heated to 120° C. After 1 hour at 120° C. the reaction solution had an NCO-content of 24.3%. When this NCO-content had been reached, the reaction mixture was treated further as in Examples 1 to 3. The reaction product (residue of the thin-film distillation) had an NCO-content of 15.3% and a monomer content of <0.7%. Its viscosity at 120° C. was 160 Pa.s and at 140° C. 63 Pa.s.

EXAMPLE 5

500 parts by wt. of TMDI, 100 parts by wt. of DMF and 2 parts by wt. of catalyst of the Ca salt of section A, were mixed and then heated to 120° C. After 45 minutes at 120° C. the reaction solution had an NCO-content of 26.7%. When this NCO-content had been reached the treatment of the reaction mixture was continued as in Examples 1 to 4. The reaction product (residue of the thin-film distillation) had an NCO-content of 16.7% and a monomer content of <0.6%. Its viscosity at room temperature was 540 Pa.s, at 40° C:90 Pa.s, at 60° C:12 Pa.s, at 80° C:3.3 Pa.s, and at 100° C:0.2 Pa.s.

EXAMPLE 6

200 parts by wt. of an isomer-mixture of 30 parts by wt. of toluylene-2,4-diisocyanate and 20 parts by wt. of toluylene-2,6-diisocyanate, 30 parts by wt. of DMF and 0.4 parts by wt. of catalyst as in section A, were mixed and heated to 80° C. for 30 minutes. After this time the NCO-content of this solution was 26.6%, i.e., about 75% of the isocyanate being trimerized had reacted. The viscosity of this solution at 25° C. was 0.61 Pa.s.

EXAMPLE 7

1000 parts by wt. of 5-methyl-nonamethylene diisocyanate-1,9 (MNDI), 200 parts by wt. of DMF and 2 parts by wt. of catalyst as in A, were mixed and then heated to 130° C. After about 3 hours at 130° C. the NCO-content of the reaction solution was 18.5%. When this NCO-content had been attained, the reaction mixture was cooled to 60° C. and, as already described in Examples 1 to 3, freed of solvent (DMF). The nearly DMF-free MNDI-containing MNDI isocyanurate mixture was then subjected to thin-film evaporation at 190° C./6.7 Pa. The reaction product (distillation residue) had an NCO-content of 15.4%, a monomer content of <0.7% and a viscosity at 25° C. of 5.7 Pa.s, at 40° C. of 1.8 Pa.s and at 60° C. of 0.6 Pa.s.

Figure 2:
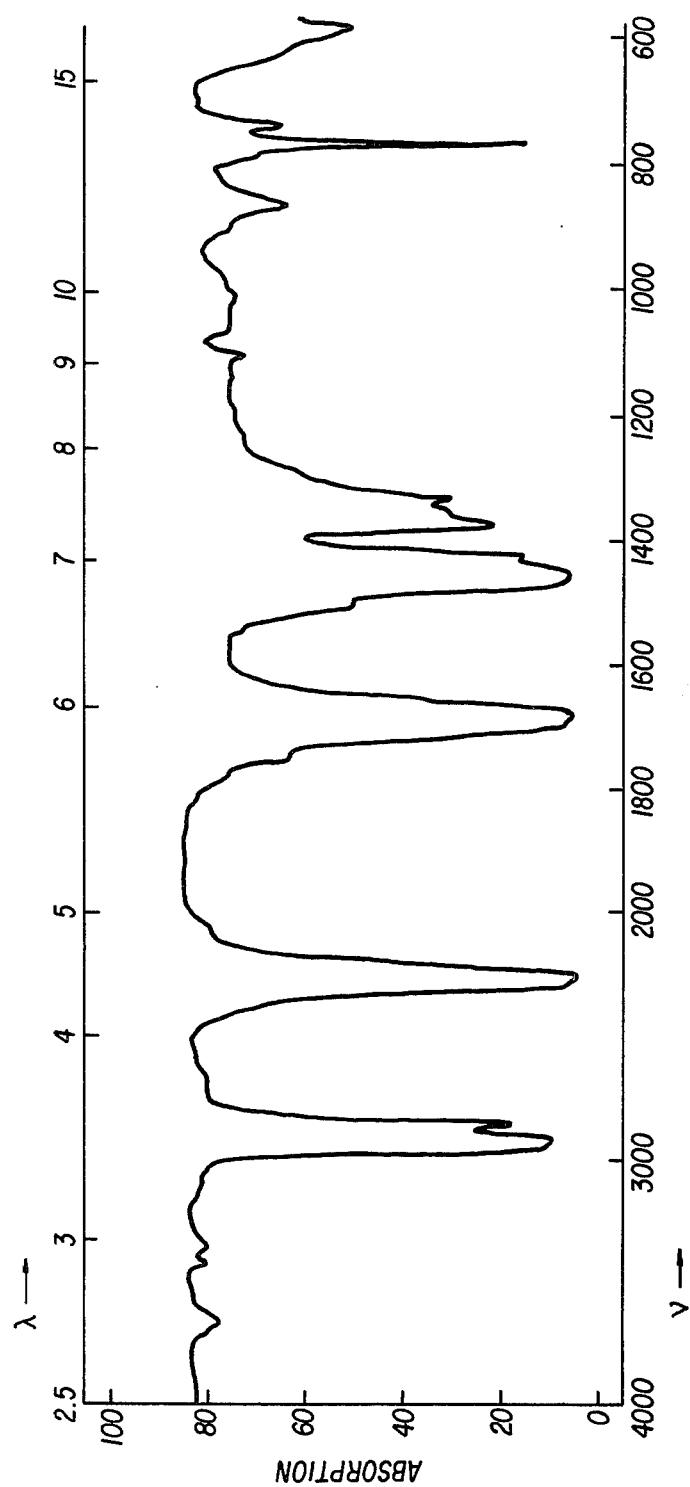
FIG. 2 is the infra-red spectrum of the trimer obtained by Example 7.

The IR-spectrum of the reaction product is shown in FIG. 2.

What is claimed as new and desired to be secured by Letters Patent of the United States:

1. A method of preparing 2, 4, 6-triketohexahydrotriazines which comprises:
    catalytically trimerizing an organic isocyanate at 60°–150° C. in an inert, polar solvent present in an amount of 5–40% by weight with respect to the quantity of said isocyanate, in the presence of 0.1–5 weight % of a catalyst of the formula:

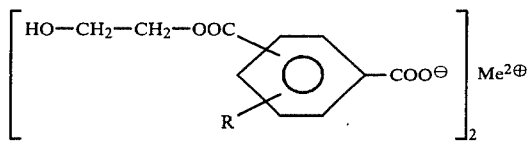

or hydrated derivatives of said catalyst, wherein R is selected from the group consisting of hydrogen and $C_1$–$C_4$ alkyl, and $Me^{2+}$ is a bivalent metal cation;
    interrupting the trimerization at a conversion of about 50%, by cooling said trimerization, and then isolating said 2, 4, 6-triketohexahydrotriazine.

2. The method of claim 1 wherein the temperature is 80°–130° C.

3. The method of any of claims 1 or 2 wherein the 2, 4, 6-triketohexahydrotriazine is isolated by subjecting the mixture to thin-film distillation thereby separating unreacted isocyanate.

4. The method of any of claims 1–2 wherein the isocyanates are selected from the group consisting of 3-isocyanatomethyl-3, 5, 5-trimethyl cyclohexyl isocyanate, 2,4-toluylene diisocyanate and mixtures thereof.

5. The method of claim 1 wherein said solvent is selected from the group consisting of dimethyl formamide, dimethyl sulfoxide and hexamethyl phosphoric triamide.

6. The method of any of claims 1 or 5 wherein said solvent is used in an amount of from 10–20% with respect to the quantity of said isocyanate.

* * * * *